United States Patent [19]

Grabowski et al.

[11] Patent Number: 5,490,990
[45] Date of Patent: Feb. 13, 1996

[54] PRODUCTION OF SOLID PHARMACEUTICAL DEPOT FORMS

[75] Inventors: Sven Grabowski, Ludwigshafen; Astrid Kah-Helbig, Neustadt; Axel Sanner, Frankenthal; Kurt Wendel, Ludwigshafen, all of Germany

[73] Assignee: BASF Aktiengesellschaft, Ludwigshafen, Germany

[21] Appl. No.: 78,824

[22] Filed: Jun. 21, 1993

[30] Foreign Application Priority Data

Jun. 25, 1992 [DE] Germany ............... 42 20 782.7

[51] Int. Cl.⁶ ............... A61K 47/32; A61K 9/20
[52] U.S. Cl. ............... 424/486; 514/772.5; 514/772.6; 514/781; 424/465
[58] Field of Search ............... 424/486, 465; 514/772.5, 772.6, 781; 523/342

[56] References Cited

U.S. PATENT DOCUMENTS

| | | |
|---|---|---|
| Re. 27,107 | 3/1971 | Levesque . |
| 3,784,648 | 1/1974 | Bergmeister et al. . |
| 4,540,602 | 9/1985 | Motoyama et al. ............ 424/494 |
| 4,737,357 | 4/1988 | Lehmann et al. ............ 424/487 |
| 4,859,751 | 8/1989 | Schulce et al. . |
| 4,892,910 | 1/1990 | Klesse et al. ............ 525/221 |
| 5,017,631 | 5/1991 | Rauch et al. ............ 523/340 |
| 5,025,004 | 6/1991 | Wu et al. ............ 514/165 |

FOREIGN PATENT DOCUMENTS

| | | |
|---|---|---|
| 263379 | 2/1963 | Australia ............ 523/342 |
| 0142877 | 5/1985 | European Pat. Off. . |
| 0536595 | 4/1993 | European Pat. Off. . |
| 3143071 | 5/1983 | Germany . |
| 3923229 | 1/1991 | Germany . |

*Primary Examiner*—Peter F. Kulkosky
*Attorney, Agent, or Firm*—Oblon, Spivak, McClelland, Maier & Neustadt

[57] ABSTRACT

A process for the production of solid pharmaceutical depot forms by application of a reconstituted aqueous dispersion of a pharmaceutically acceptable binder to a core which contains active substance or by wet granulation of the pharmaceutical active substance with such a binder dispersion or by direct tableting of an active substance with the redispersible binder powder, wherein the binder has been obtained by emulsion polymerization and subsequent spray drying of the resulting aqueous dispersion with a water-soluble pharmaceutically acceptable spraying aid with a glass transition temperature of at least 60° C. and with or without a pharmaceutically acceptable antiblocking agent.

18 Claims, No Drawings

PRODUCTION OF SOLID PHARMACEUTICAL DEPOT FORMS

The present invention relates to the production of solid pharmaceutical depot forms using a powder (for direct tableting) or using an aqueous dispersion, which has been reconstituted therefrom by stirring with water, of a binder which has been obtained by spray drying a binder dispersion, which has been obtained by emulsion polymerization, in the presence of 5–50% by weight, based on the binder, of a water-soluble spraying aid with a glass transition temperature Tg of at least 60° C. The powder preferably also contains an antiblocking agent.

Redispersible polymer powders can be produced from aqueous polymer dispersions by spraying the dispersions, using single-component or multicomponent nozzles, into a stream of hot air. This is successful when the glass transition temperature of the polymer is sufficiently high, ie. above 50° C. Otherwise blocking occurs, usually even during spraying, but at the latest during storage, especially on exposure to heat and/or pressure. This adversely affects the redispersibility of the polymer powder.

Attempts have been made to prevent blocking by adding protective colloids or inert substances to polymers which have relatively low glass transition temperatures. Although the redispersibility of the resulting polymer powders was better, the properties of the coatings produced from these mixtures were debased.

The use of spraying aids in spray drying is conventional and described, for example, in DE 20 49 114, 31 43 071, 33 44 242 and 39 23 229. In these, no thought was given to use in the production of drugs. Accordingly, no attention was paid to the physiological tolerability of the aids.

It is an object of the present invention to provide a redispersible powder from which it is possible to reconstitute, without any chemical or physical aids, only by stirring with water, a dispersion which can be employed for wet granulation of pharmaceutical active and ancillary substances to produce depot matrix tablets. It should also be possible to produce the latter by direct tableting of the active substance (with or without other ancillary substances) with the redispersible powder. Furthermore, it should be possible to employ the redispersible powder (in the form of a reconstituted dispersion) also for coating active substance-containing cores. Finally, the reconstituted dispersion should be compatible with pigments and other conventional pharmaceutical ancillary substances.

In the production of depot matrix tablets, the active substance is embedded together with water-soluble ancillary substances in water-insoluble, non-digestible (inert) ancillary substances which form a framework. Pores are produced when the soluble constituents dissolve out, and the active substance diffuses through them to the outside. The inert substances employed to form the framework are mainly polymers such as polyvinyl chloride, polyethylene, polyamides, silicones, ethylcelluloses and methacrylate/acrylate copolymers. The mixture of active and ancillary substances is compressed either directly or after wet granulation with binder solutions. The kinetics of release of the active substance can be controlled by means of the content of insoluble polymer.

Water-insoluble polymers are employed for wet granulation advantageously in the form of dispersions obtained by emulsion polymerization. Emulsion polymers contain water-insoluble, submicroscopic latex particles and have a relatively low viscosity even at a high solids content (up to 40% by weight), so that relatively large amounts of release-slowing polymeric substances can be incorporated in conventional wet granulation. The use of aqueous dispersions dispenses with all the problems caused by organic solvents because of their flammability, toxicity and environmental pollution.

Redispersible powders are particularly desirable for this purpose because, on the one hand, they allow the matrix tablet to be produced by direct tableting of the active substance with the powdered emulsion polymer and, on the other hand, there is elimination of all the problems associated with the use of latices, such as microbial and chemical contamination, coagulation on exposure to low or high temperatures, skinning, sedimentation and, last but not least, high transport costs.

Advantageous for the formation of a coherent matrix are soft polymers, ie. those with a low glass transition temperature Tg. However, it is precisely emulsion polymers of this type which give rise to difficulties, as mentioned, on spray drying. The known spraying aids do not meet pharmaceutical requirements.

We have found that this object is achieved in that water-soluble polymers with a glass transition temperature of at least 60° C. of natural or synthetic origin, which are already employed in pharmaceutical technology, are outstandingly suitable as spraying aids, and moreover do not adversely affect the resulting depot system in such a way that, for example, it is no longer possible greatly to slow the release of an active substance which is readily soluble in water. We have also found that water-insoluble ancillary substances conventional in pharmaceutical technology, predominantly inorganic in nature, are excellent as antiblocking agents in the dispersible powder obtained by spray drying with the spraying aid.

The object on which the invention is based is therefore achieved by the process set forth in the claims.

The powder systems obtainable according to the invention and composed of emulsion polymer, spraying aid and antiblocking agent can be employed for wet granulation by reconstituting the dispersion by stirring the powder with water with or without the addition of pigments and/or other conventional pharmaceutical aids and with or without heating, and spraying the dispersion onto a powdered active substance or a powdered mixture of active and ancillary substances. However, the powder systems can also be employed for direct tableting, ie. for direct compression of the polymer powder with the pharmaceutical active substance, with or without other ancillary substances.

The invention starts from aqueous polymer dispersions produced by emulsion polymerization of ethylenically unsaturated compounds using free radical initiators in the presence of conventional additives.

Examples of suitable ethylenically unsaturated monomers are $C_1$-$C_{18}$-alkyl (meth)acrylates, such as methyl methacrylate and ethyl acrylate, also hydroxyalkyl (meth)acrylates, vinyl esters and vinyllactams; furthermore unsaturated mono- or dicarboxylic acids such as (meth)acrylic acid, maleic, fumaric and itaconic acid, as well as monoesters or monoamides of these diacids. Suitable monomers with basic groups are N-vinylimidazole, N-vinylimidazoline, N-vinylimidazolidine, N-vinylpyridine, monoalkyl or dialkylaminoalkyl esters or monoalkyl- or dialkylaminoalkylamides of unsaturated polymerizable carboxylic acids. It is likewise possible to employ anionic monomers such as salts of acrylamidoalkylsulfonic acids, cationic monomers such as trimethylammonioethyl methacrylate chloride, crosslinking monomers such as methylol(meth)acrylamides and derivatives thereof.

The choice of the monomers or of the monomer mixtures depends, on the one hand, on the requirements of the coating process (glass transition temperature, minimum film-forming temperature) and, on the other hand, on the pharmaceutical behavior of the coating (solubility in various media, hardness, brittleness or elasticity of the film and its permeability for the active substance).

Free radical polymerization initiators which can be used are the conventional ones such as hydrogen peroxide, organic peroxides and hydroperoxides, with or without the presence of reducing compounds such as ascorbic acid, water-soluble azo compounds such as 2,2-azobis(2-amidinopropane) dihydrochloride, as well as inorganic peroxides such as alkali metal or ammonium salts of peroxidisulfuric acid in amounts of about 0.1–2% of the total weight of the monomers.

If required, other conventional ancillary substances can be added to the polymerization mixture. These ancillary substances include seed latices which improve the reproducibility of the particle size of the final products, and buffers, complexing agents, dispersants and emulsifiers. The emulsion polymers, as a rule, are produced in the presence of anionic, cationic or non-ionic emulsifiers or the compatible mixtures thereof in the form of an aqueous latex with a solids content of 20 –70, preferably 30–60, % by weight.

The spray drying is carried out in a conventional way in spray towers, it being possible for the dispersion to be sprayed in by means of diffusing disks or single-component or multicomponent nozzles. The dispersion is dried with hot gases, eg. nitrogen or air. When obtaining the dry polymer powder from the latex, care must be taken that the latex particles remain as such and do not form aggregates.

Added as spraying aids are one or more water-soluble substances with a second order phase transition point (glass transition temperature Tg) of at least 60° C. in amounts of 5–50%, preferably 10–30%, of the weight of the emulsion polymer employed as binder. Water-soluble polymeric substances, especially those with high degrees of polymerization, have proven suitable for this.

To achieve good redispersibility, it has proven suitable for the total of the amount of protective colloid used in the production of the dispersions, and of the amount of spraying aid to be at least 6% by weight, preferably 10–30% by weight. The upper limit may be regarded as 50, preferably 40, % by weight.

The spraying aid to be used according to the invention must be pharmaceutically (physiologically) acceptable. Suitable examples are ancillary substances which are described in pharmacopeia monographs or have been used for many years without incidents or are authorized for use in foodstuffs (see, for example, Katalog pharmazeutischer Hilfsstoffe, compiled by a working party from Ciba-Geigy, Hoffmann-LaRoche and Sandoz; Pharmazeutische Technologie by H. Sucker, P. Fuchs and P. Speiser, Thieme Verlag, 1991, Chapter 5, and the literature cited therein; Überzugsstoffe und Trennmittel, Lebensmittelchem. Gesellschaft - Fachgruppe der GDCh, Behr's Verlag 1990). Examples which may be mentioned are: Cellulose derivatives such as methylcellulose, hydroxypropylcellulose, hydroxyethylcellulose, hydroxypropylmethylcellulose, carboxymethylcellulose sodium (described in all pharmacopeias) polyvinylpyrrolidones (mentioned, for example, in USP/NF XVI), copolymers of N-vinylpyrrolidone and vinyl acetate in the ratio 60:40 by weight (DAB Copolyvidon monograph), starch derivatives (modified starches complying with the Foodstuffs and Consumables Act) and polyvinyl alcohols (especially purified grades for pharmaceutical purposes, average molecular weights from 30,000 to 200,000).

To improve the storability, ie. prevent caking and blocking of powders with a low glass transition temperature, and thus to improve the redispersibility, the resulting powder is mixed with conventional antiblocking agents in an amount of 0–50%, preferably 5–25%, of the total weight of the polymeric components. This is preferably carried out while the powder is still finely dispersed, ie. still suspended in the dry gas. It is advantageous to meter these agents into the drying apparatus spatially separate from but at the same time as the dispersion. Substances with an average particle size of 0.1–50 μm are particularly suitable.

The antiblocking agent must, of course, likewise be pharmaceutically acceptable (see above). Examples which may be mentioned are:

Colloidal silicon dioxide (described in NF XIII), talc, calcium, magnesium and sodium carbonates, tricalcium orthophosphate, magnesium orthophosphate, microcrystalline cellulose and magnesium stearate. They are described in pharmacopeias and are authorized for use in foodstuffs.

EXAMPLES 1–6

Spray drying

An aqueous dispersion of an ethyl acrylate/methyl methacrylate emulsion copolymer (2:1 mol, Tg about 7° C., minimum film-forming temperature (DIN 53 787) about 4° C., viscosity about 5 mPa.s) with a solids content of 30% by weight was spray dried with a spraying aid and with addition of the required amount of antiblocking agent. Examples 1–6 are summarized in Table 1. All percentage data are based on the weight of the emulsion polymer.

TABLE 1

| Example | Spraying aid | Antiblocking agent | Temperatures in °C. | | |
|---|---|---|---|---|---|
| | | | Inlet | Outlet | Nozzle |
| 1 | Copolymer of 60% VP[1] + 40% VAc[2] (20%) | Talc (10%) | 90–100 | 60–70 | 10 |
| 2 | Copolymer of 60% VP[1] + 40% VAc[2] (20%) | Tricalcium orthophosphate (10%) | 90–100 | 60–70 | 10 |
| 3 | Degraded starch (20%) | Talc (10%) | 90–95 | 65–68 | 10 |
| 4 | Degraded starch (20%) | Tricalcium orthophosphate (10%) | 90–95 | 65–68 | 10 |
| 5 | Hydroxypropylmethylcellulose (20%)[4] | Unnecessary | 90–100 | 60–70 | 25 |
| 6 | Polyvinylpyrrolidone (30%) | Talc (10%) | 110–120 | 65–75 | 25 |

[1] N-vinylpyrrolidone
[2] Vinyl acetate
[3] Snowflake ®901910, Cerestar, Krefeld
[4] Pharmacoat ®606, Shin-Etsu Chemical, Tokyo The resulting powders were still free-flowing and redispersible by stirring with cold water after 8 months at 25° C.

EXAMPLE 7

An aqueous dispersion of a vinyl acetate emulsion polymer with a viscosity of about 5 mPa.s and with a solids content of 30% by weight was spray dried with 30% by weight, based on the polymer, of polyvinylpyrrolidone. Inlet at 120°–130° C., outlet at 80°–90° C., nozzle at 16° C.

EXAMPLE 8

Wet granulation

Matrix tablets were produced using a reconstituted aqueous dispersion of the polymer powder obtained as in Example 3 and with the following formula:

1. Composition

| I | Theophylline | 125 g |
|---|---|---|
|  | Ca hydrogen phosphate | 75 g |
| II | Polymer powder (Example 3) as 30% strength aqueous dispersion | 10 g |
|  | Water | 31 g |
|  | Talc | 1 g |
| III | Magnesium stearate | 1 g |

The redispersion of the polymer powder according to the invention was carried out simply by stirring into cold water.

The mixture I was granulated with dispersion II in a fluidized bed granulator, then mixed with III and compressed to tablets in a rotary machine under a pressure of 9.3 kN.

2. Physical properties of the tablets

| Weight | 211.82 mg |
|---|---|
| Hardness by DAB method | 64 N |
| Friability by DAB method | 0.3% |

3. Theophylline release

The theophylline release was determined by the US Pharmacopeia XXII paddle method at 50 rpm, comparing with an identically produced matrix tablet with a commercial ethyl acrylate/methyl methacrylate copolymer (Eudragit NE 30 D, Röhm Pharma, 30% strength dispersion).

Medium: aqueous buffer solution of pH 7.4

| Time | Eudragit NE 30 D | Polymer powder of Example 3 |
|---|---|---|
| 1 h | 23.9 | 26.5 |
| 2 h | 40.1 | 45.4 |
| 3 h | 51.0 | 59.3 |
| 5 h | 65.7 | 77.7 |
| 8 h | 81.1 | 95.7 |

Result: Very similar release in both cases, ie. the depot form produced according to the invention is equivalent to the prior art.

EXAMPLE 9

Wet granulation

Matrix tablets were produced using a reconstituted aqueous dispersion of the polymer powder obtained as in Example 7 and with the following formula:

1. Composition

| I | Theophylline | 125 g |
|---|---|---|
|  | Lactose | 75 g |
| II | Polymer powder (Example 7) as 30% strength aqueous disperison | 10 g |
|  | Water | 31 g |
|  | Talc | 1 g |
| III | Magnesium stearate | 1 g |

The redispersion of the polymer powder according to the invention was carried out simply by stirring into cold water.

The mixture I was granulated with dispersion II by hand, then mixed with III and compressed to tablets in a rotary machine under a pressure of 9.3 kN.

2. Physical properties of the tablets

| Weight | 219 mg |
|---|---|
| Hardness by DAB method | 73 N |
| Friability by DAB method | 0.25% |

3. Theophylline release

The release was determined as in Example 8.

| Time | Eudragit NE 30 D | Polymer powder of Example 7 |
|---|---|---|
| 1 h | 21.6 | 17.4 |
| 2 h | 32.6 | 26.5 |
| 4 h | 48.1 | 39.9 |
| 6 h | 58.7 | 48.8 |
| 8 h | 66.0 | 56.7 |

We claim:

1. A process for the production of solid pharmaceutical depot forms by application of an aqueous dispersion, reconstituted by the addition of water to a pharmaceutically acceptable binder, to a core which contains active substance, wherein the binder is prepared by emulsion polymerization of an ethylenically unsaturated compound selected from the group consisting of $C_{1-18}$ alkyl(meth)acrylates, hydroxyalkyl(meth)acrylates, vinyl esters, vinyl lactams, mono- or dicarboxylic acids, monoesters or monoamides of these acids, N-vinylimidazole, N-vinylimidazoline, N-vinylimidazolidine, N-vinylpyridine, monoalkyl- or dialkylaminoalkyl esters or monoalkyl- or dialkylaminoalkylamides of polymerizable carboxylic acids, acrylamidoalkylsulfonic acids, trimethylammonioethyl methacrylate chloride and methylol(meth)acrylamides, which produces a water insoluble polymer, and subsequent spray drying of the resulting aqueous polymer dispersion with 5–50% by weight of a water-soluble pharmaceutically acceptable spraying aid selected from the group consisting of cellulose derivatives, polyvinylpyrrolidones, copolymers of N-vinylpyrrolidone and vinylacetate, starch derivatives and polyvinylalcohols with a glass transition temperature of at least 60° C. and 0–50% by weight, based on the amount of binder, of a pharmaceutically acceptable antiblocking agent, the solid pharmaceutical depot forms exhibiting undiminished release properties of the active substance of the core.

2. A process for the production of solid pharmaceutical depot forms by wet granulation of a pharmaceutically active substance, with a aqueous binder dispersion, which has been reconstituted by the addition of water to a binder, wherein the binder is prepared by emulsion polymerization of an ethylenically unsaturated compound selected from the group consisting of $C_{1-18}$ alkyl(meth)acrylates, hydroxyalkyl(meth) acrylates, vinyl esters, vinyl lactams, mono- or dicarboxylic acids, monoesters or monoamides of these acids, N-vinylimidazole, N-vinylimidazoline, N-vinylimidazolidine, N-vinylpyridine, monoalkyl- or dialkylaminoalkyl esters or monoalkyl- or dialkylaminoalkylamides of polymerizable carboxylic acids, acrylamidoalkylsulfonic acids, trimethylammonioethyl methacrylate chloride and methylol(meth)acrylamides, which produces a water insoluble polymer, and subsequent spray drying of the resulting aqueous polymer dispersion with 5–50% by weight of a water-soluble pharmaceutically acceptable spraying aid selected from the group consisting of cellulose derivatives, polyvinylpyrrolidones, copolymers of N-vinylpyrrolidone and vinylacetate, starch derivatives and polyvinylalcohols with a glass transition temperature of at least 60° C. and 0–50% by weight, based on the amount of binder, of a pharmaceutically acceptable antiblocking agent, the solid pharmaceutical depot forms exhibiting undiminished release properties of the active substance.

3. A process for the production of drug tablets by direct tabletting of an active substance and 5–99.9% by weight of a conventional pharmaceutical aid, wherein 5–95% by weight, based on the tablet, of a binder powder is prepared by emulsion polymerization of an ethylenically unsaturated compound selected from the group consisting of $C_{1-18}$ alkyl(meth)acrylates, hydroxyalkyl(meth)acrylates, vinyl esters, vinyl lactams, mono- or dicarboxylic acids, monoesters or monoamides of these acids, N-vinylimidazole, N-vinylimidazoline, N-vinylimidazolidine, N-vinylpyridine, monoalkyl- or dialkylaminoalkyl esters or monoalkyl- or dialkylaminoalkylamides of polymerizable carboxylic acids, acrylamidoalkylsulfonic acids, trimethylammonioethyl methacrylate chloride and methylol-(meth)acrylamides, which produces a water insoluble polymer, and subsequent spray drying of the resulting aqueous polymer dispersion with 5–50% by weight of a water-soluble pharmaceutically acceptable spraying aid selected from the group consisting of cellulose derivatives, polyvinylpyrrolidones, copolymers of N-vinylpyrrolidone and vinylacetate, starch derivatives and polyvinylalcohols with a glass transition temperature of at least 60° C. and 0–50% by weight, based on the amount of binder, of a pharmaceutically acceptable antiblocking agent, the solid tablets exhibiting undiminished release properties of the active substance.

4. The process of claim 1, wherein from 5–50% by weight of antiblocking agent selected from the group consisting of colloidal silicon dioxide, talc, calcium, magnesium or sodium carbonate, tricalcium orthophosphate, magnesium orthophosphate, microcrystalline cellulose and magnesium stearate is present.

5. The process of claim 2, wherein from 5–50% by weight of antiblocking agent selected from the group consisting of colloidal silicon dioxide, talc, calcium, magnesium or sodium carbonate, tricalcium orthophosphate, magnesium orthophosphate, microcrystalline cellulose and magnesium stearate is present.

6. The process of claim 3, wherein from 5–50% by weight of antiblocking agent selected from the group consisting of colloidal silicon dioxide, talc, calcium, magnesium or sodium carbonate, tricalcium orthophosphate, magnesium orthophosphate, microcrystalline cellulose and magnesium stearate is present.

7. A process for the production of solid pharmaceutical depot forms as claimed in claim 1, wherein the emulsion polymer employed as binder is comprised of vinyl acetate.

8. A process for the production of solid pharmaceutical depot forms as claimed in claim 2, wherein the emulsion polymer employed as binder is comprised of vinyl acetate.

9. A process for the production of solid pharmaceutical depot forms as claimed in claim 3, wherein the emulsion polymer employed as binder is comprised of vinyl acetate.

10. A process for the production of solid pharmaceutical depot forms as claimed in claim 1, wherein the emulsion polymer employed as binder is comprised of ethyl acrylate and methyl methacrylate in the ratio 2:1 by weight.

11. A process for the production of solid pharmaceutical depot forms as claimed in claim 2, wherein the emulsion polymer employed as binder is comprised of ethyl acrylate and methyl methacrylate in the ratio 2:1 by weight.

12. A process for the production of solid pharmaceutical depot forms as claimed in claim 3, wherein the emulsion polymer employed as binder is comprised of ethyl acrylate and methyl methacrylate in the ratio 2:1 by weight.

13. A process for the production of solid pharmaceutical depot forms as claimed in claim 1, wherein the spray-dried emulsion polymer employed as binder contains a water-soluble N-vinylpyrrolidone polymer which contains 0–50% by weight of vinyl acetate as copolymerized units.

14. A process for the production of solid pharmaceutical depot forms as claimed in claim 2, wherein the spray-dried emulsion polymer employed as binder contains a water-soluble N-vinylpyrrolidone polymer which contains 0–50% by weight of vinyl acetate as copolymerized units.

15. A process for the production of solid pharmaceutical depot forms as claimed in claim 3, wherein the spray-dried emulsion polymer employed as binder contains a water-soluble N-vinylpyrrolidone polymer which contains 0–50% by weight of vinyl acetate as copolymerized units.

16. A process for the production of solid pharmaceutical depot forms as claimed in claim 1, wherein a water-soluble polysaccharide is employed as spraying aid.

17. A process for the production of solid pharmaceutical depot forms as claimed in claim 2, wherein a water-soluble polysaccharide is employed as spraying aid.

18. A process for the production of solid pharmaceutical depot forms as claimed in claim 3, wherein a water-soluble polysaccharide is employed as spraying aid.

\* \* \* \* \*